(12) United States Patent
Arnold et al.

(10) Patent No.: US 10,195,322 B2
(45) Date of Patent: Feb. 5, 2019

(54) ELECTRICAL ARRANGEMENT COMPRISING AN IMPLANTABLE CABLE ELEMENT

(71) Applicant: Berlin Heart GmbH, Berlin (DE)

(72) Inventors: Mario Arnold, Berlin (DE); Kim Peter Winterwerber, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 0 days.

(21) Appl. No.: 15/958,471

(22) Filed: Apr. 20, 2018

(65) Prior Publication Data

US 2018/0236150 A1 Aug. 23, 2018

Related U.S. Application Data

(63) Continuation of application No. 15/030,729, filed as application No. PCT/EP2014/073470 on Oct. 31, 2014, now Pat. No. 9,974,892.

(30) Foreign Application Priority Data

Oct. 31, 2013 (EP) .................................... 13191130

(51) Int. Cl.

| A61M 1/00 | (2006.01) |
| A61M 1/10 | (2006.01) |
| A61N 1/375 | (2006.01) |
| H01B 7/282 | (2006.01) |
| H01B 7/36 | (2006.01) |
| H01B 17/12 | (2006.01) |
| H02G 3/22 | (2006.01) |
| A61M 39/00 | (2006.01) |
| A61M 1/12 | (2006.01) |
| A61N 1/05 | (2006.01) |
| H01B 7/04 | (2006.01) |

(52) U.S. Cl.
CPC .......... *A61M 1/1001* (2014.02); *A61M 1/122* (2014.02); *A61M 39/00* (2013.01); *A61N 1/3752* (2013.01); *H01B 7/2825* (2013.01); *H01B 7/361* (2013.01); *H01B 17/12* (2013.01); *H02G 3/22* (2013.01); *A61M 1/1008* (2014.02); *A61M 1/12* (2013.01); *A61M 1/127* (2013.01); *A61N 1/056* (2013.01); *A61N 1/3754* (2013.01); *H01B 7/048* (2013.01)

(58) Field of Classification Search
CPC ........................... A61M 1/1001; A61M 1/122
USPC ......................................................... 600/16
See application file for complete search history.

(56) References Cited

U.S. PATENT DOCUMENTS

2007/0129779 A1 6/2007 Ayre et al.
2013/0190551 A1 7/2013 Callaway et al.

FOREIGN PATENT DOCUMENTS

| WO | WO 94/01175 | 1/1994 |
| WO | WO 00/57948 | 10/2000 |
| WO | WO 2005/075017 | 8/2005 |

*Primary Examiner* — Nadia A Mahmood
(74) *Attorney, Agent, or Firm* — Brinks Gilson & Lione

(57) ABSTRACT

An electrical arrangement with an implantable cable element may be provided which comprises a strain relief element which is arranged centrically in the cross section, as well as a group of conductors insulated to one another, said group being stranded around the strain relief element, and a common shielding element surrounding the electrical conductors, as well as a fluid-tight cable sheath. The implantable cable element may have a symmetrical construction.

17 Claims, 5 Drawing Sheets

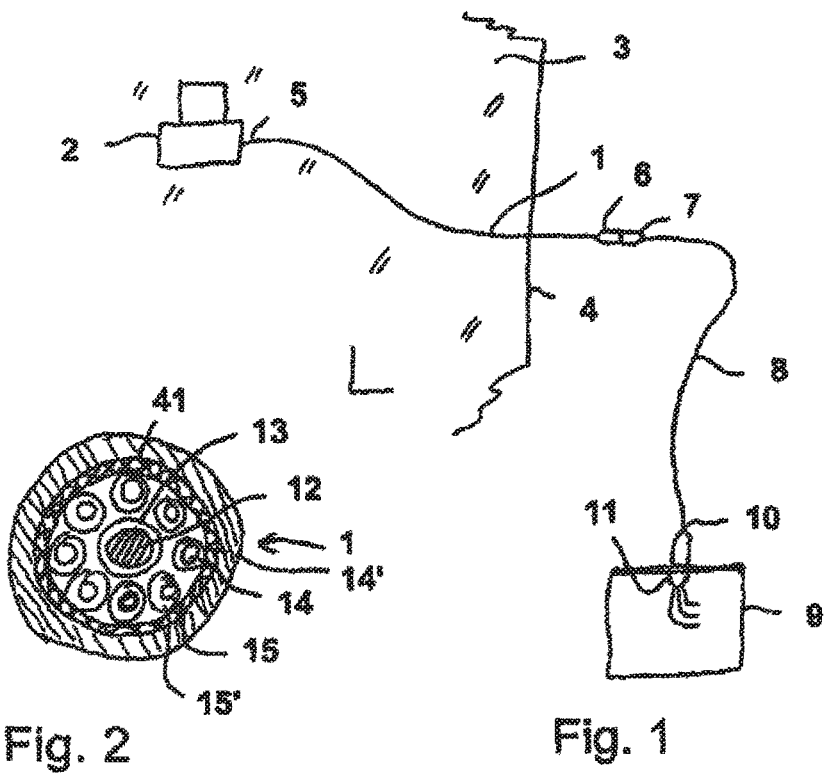
Fig. 2
Fig. 1
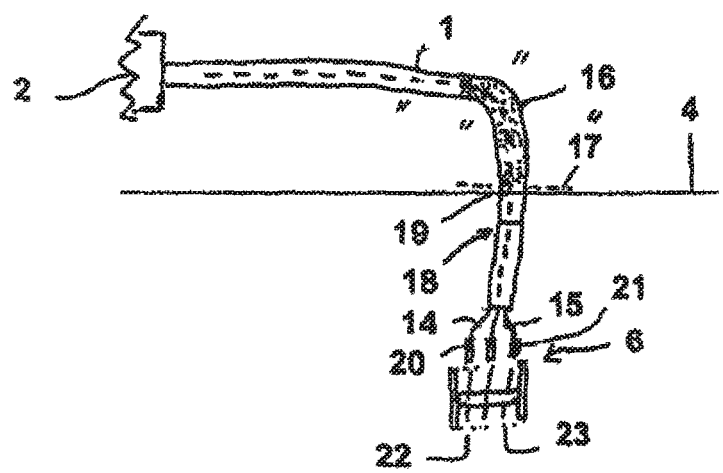
Fig. 3

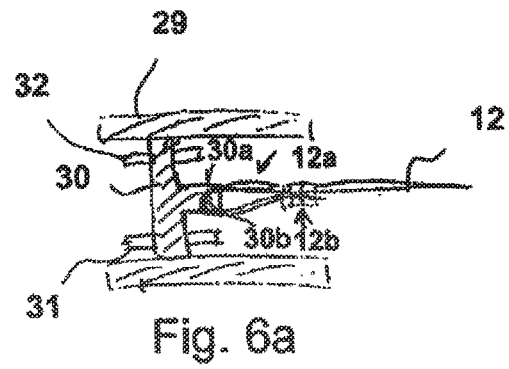
Fig. 6a
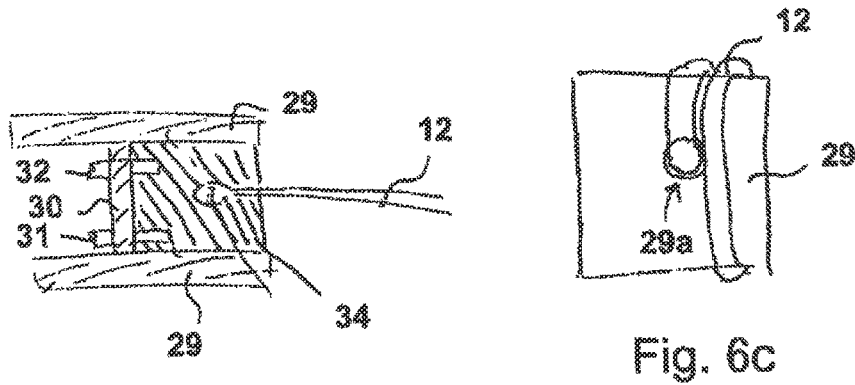
Fig. 6b
Fig. 6c
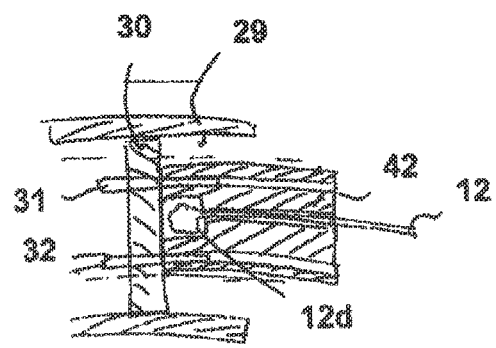
Fig. 6d

ELECTRICAL ARRANGEMENT COMPRISING AN IMPLANTABLE CABLE ELEMENT

CROSS-REFERENCE TO RELATED APPLICATIONS

This application is a continuation application of, and claims priority under 35 USC § 120 to, U.S. non-provisional application Ser. No. 15/030,729, filed Apr. 20, 2016, which is a 371 nationalization of PCT/EP2014/073470, having an international filing date of Oct. 31, 2014, which in turn claims priority under 35 USC § 119 to European patent application 13191130.7 filed on Oct. 31, 2013. The entire contents of each of the above-identified patent applications are hereby incorporated by reference.

TECHNICAL FIELD

The invention relates to the mechanical and electro-technical field and can be particularly advantageously applied to medical technology.

BACKGROUND

In medical technology, it has become possible to measure, to assist or to generally positively influence a number of body functions of a patient by way of electrical assemblies. Thus pacemakers which are electrically operated, and as well as electrical metering pumps and stimulation elements have been common for some time now, and in the more recent past, also blood pumps for assisting the heart function. Some of these electrical assemblies require a cable connection and a connection via an implantable cable to outside the body, wherein the assemblies are either connectable to an energy supply or to a control unit, or to both.

A constant loading of the implantable cable and thus high demands with regard to its service life result with the normal movements of the patient, due to the fact that many of the mentioned assemblies remain in the patient's body over a longer time period. Problems which could result for example are a breakage of the conductor (lead), wear of the conductor insulation, for example of the insulation between conductors which are led in parallel, or also a breakage or wear of a cable sheath. The conductors themselves can break due to permanent loading.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

FIG. 1 in an overview and schematically, the interaction of an implantable cable element of the electrical arrangement with an electrical assembly, a further cable element and a control unit, FIG. 2 the implantable cable element in cross section, FIG. 3 a lateral view of the implantable cable element with a plug-in connection element, FIG. 4 the plug-in connection of the implantable cable element with a further cable element in a schematic view, FIG. 5 the connection of the implantable cable element to the electrical assembly, FIGS. 6*a*-6*d* different variants of the connection of the strain relief element onto an assembly as well as FIGS. 7*a-d* different variants of markings.

DETAILED DESCRIPTION

Figure 4:
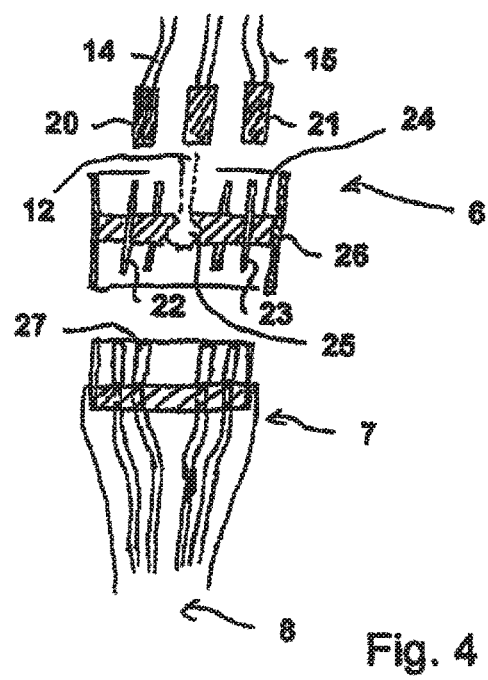

Against the background of the state of the art, it is the object of the present invention, to create an electric arrangement with an implantable cable element, which, with an as simple as possible design, permits a high reliability with a long service life.

Accordingly, a first aspect of the invention relates to an electric arrangement with an implantable cable element which comprises a strain relief element which is arranged centrically in the cross section, as well as a group of conductors insulated to one another and which is stranded around the strain relief element, and a common electrical shielding element surrounding the electrical conductors, as well as a fluid-tight cable sheath.

Until now, it is not common to apply designs with separate strain relief elements as are known for example with heavy load cables, for implantable cable elements. However, experience has shown that with heart assist pumps for example, cable breakages or damage to the cable sheath occur relatively often in the course of the operational time.

The design of the cable element and which is according to the invention firstly permits the separation on the one hand of the electric conducting function, i.e. the function of transmitting electrical energy and signals, and on the other hand of the mechanical stabilising function which is assumed by the strain relief element. The cross-sectional design of the cable envisages the strain relief element in the centre of the cross section of the cable element, said cable element being largely neutral with regard to tension, so that the strain relief element can be designed for example as a solid, restiform component. The strain relief element however for its part can also consist of stranded elements. A stranding of conductors which are distributed about the strain relief element, symmetrically in the ideal case, creates a flexibility of the cable element in all directions, without excessive tensile or compressive loads acting upon the conductors. The shorter the pitch of the stranding, the more easily flexible does the cable element become. The individual conductors for example can serve for the electric energy supply of a motor of a pump (for example three conductors) as well as for the supply of a magnetic bearing (for example two conductors) and for example also for the supply of pump electronics (two conductors). Conductors for communication can additionally be provided. The individual conductors can in each case consists of one or more groups of strands which for their part for example are also stranded. The strands for their part can be constructed for example in different concentric layers which are stranded in each case in opposite directions. Occurring tangential forces are compensated by this in the case of a bending of a conductor.

The individual conductors are provided in each case with a conductor insulation, wherein the material of the insulation is selected in a manner such that the adhesive friction of the conductor insulations to one another is minimised. A suitable material for this is polytetraflourethylene (PTFE) for example.

The strain relief element can also be surrounded by a PTFE layer, for example bandaged with a PTFE tape, in order to permit a good sliding of the conductors on the strain relief element.

As a whole, it makes sense to design the cable construction symmetrically in cross section, and to also construct parts of the cable, for example individual conductors, symmetrically per se.

A copper alloy can be used as a material for the conductors, specifically for the individual strand wires of the conductors, or a construction of a silver core with an outer layer of a nickel-cobalt base alloy. Each individual conductor in its outer region can be galvanically covered with a silver layer or gold layer, in order to minimise corrosion processes within the cable element.

Particular advantages of the invention are released by way of the cable element within the framework of an electrical arrangement being fixedly connected in an electrical and mechanical manner to an implantable electric assembly, in particular to a blood pump.

One deliberately makes do without a plug-in connection in this region, in order there to be able to realise a high reliability of the connection with a simple sealing ability and an optimal electrical shielding of the connection. The connection between the cable element and the assembly, in particular the blood pump, is created before the implantation. In practise, very seldom does an advantage of being able to exclusively exchange the electrical assembly without the implantable cable element arise. The cable element itself, on account of the invention, should be designed in such a stable manner that it is subjected to no damage during the expected operational time. The cable sheath of the cable element is advantageously connected to the housing of the assembly in a fluid-tight manner by way of welding, moulding or bonding. The conductors are advantageously connected to conductors of a feed-through of the assembly housing by way of clamping or soldering.

Advantageously, one can moreover envisage the implantable cable element comprising a plug-in connection element for the connection to a second cable element.

The plug-in connection element is usually provided outside the implanted region of the cable element, so that after implantation, a further cable can be connected to the implantable cable element and also electrically released from this again without any problem. If damage occurs in this region, then this can be overcome also without any operative intervention with regard to the patient.

The invention can moreover be advantageously designed such that the cable sheath of the implantable cable element in sections comprises a layer promoting the ingrowth of tissue, and that in particular this layer is distanced to a plug-in connection element in the longitudinal direction of the cable end.

The cable sheath of the cable element can consist of a plastic in the implantable region. The most important demands are biocompatibility as well as mechanical stability and wear resistance. Moreover, the cable element should also have a high UV-resistance in the non-implantable region of this.

Materials which are considered for example are polyurethane and silicones. The implantable cable element for example can be protected by a textile coating in the non-implantable or non-implanted region.

The region which favours or encourages the ingrowth of tissue can have a roughened, velour-like surface.

The material of the cable sheath can also be designed as a composite material with reinforcement, for example by way of tensionally strong aramide fibres, glass fibres or a metal wire mesh, for the further stabilisation.

Usually, an electrical shielding which can be designed for example as a mesh of metal wires, for example silver-coated copper wires, or as a metal-coated plastic non-woven is provided between the conductors of the implantable cable element which are arranged centrically inwards with regard to the cross section, and the cable sheath. Particularly advantageously, a combination of a metallised plastic non-woven and a metal woven fabric can also be used. A metal wire mesh in the cable sheath can also serve as a shielding. The so-called transfer impedance of the cable element can be optimised by way of an optimised selection of the shielding.

An aspect of the invention envisages the layer promoting the ingrowth of tissue in particular being distanced to the plug-in connection element in the longitudinal direction of the cable end.

It is useful to achieve an as good as possible intergrowth of body tissue with the cable sheath, in order to minimise the migration of germs through the skin into the body of the patient, in the region of the feed-through of the cable element. Aspects of the topography of the surface (porosity, macrostructure), of the elasticity of the surface and of a functional task of the surface are important with regard to this. An increased probability of cell adhesion results due to a structured surface which is structured by way of pores for example, so that the ingrowth is encouraged. A reduced elasticity of the cable sheath surface moreover favours the ongrowth of cells.

The concentration upon the structuring of the surface has been found to be particularly advantageous, in order to obtain a good flexibility with a low design effort, since the elasticity of the cable sheath surface is not freely selectable. Additional functional tasks of the sheath surface are conceivable.

One envisages the structured region of the cable sheath which represents a layer promoting the ingrowth of tissue, only extending a little beyond the length region of the cable element which is envisaged for implanting, and at all events ending before the plug-in connection element and being distanced to this, in the axial direction, in order to prevent the migration of germs along the cable sheath surface. In a preferred variant, the structured region does not project beyond the length region of the cable sheath which is envisaged for implantation, so that the layer promoting the ingrowth of tissue can be arranged completely within the body.

The invention can moreover advantageously be designed such that the strain relief element consists of a metal, in particular stainless steel.

A variant of the strain relief element of aramide fibres or other tensionally strong fibres, in particular plastic fibres is also possible. Further fibre materials can for example be carbon, or dyneema or fibre mixtures of the three above-mentioned fibres. Stainless steel combines a high tensile strength with a low initial extension. The connection of the strain relief element onto the electrical assembly on the one hand, and a plug-in connection element onto the ends of the cable element on the other hand is moreover particularly simple with the use of stainless steel. High-strength plastic fibres have a comparable tensile strength and are moreover less prone to corrosion and more flexible that stainless steel.

The strain relief element can advantageously be fastened on a housing of the electric assembly, in particular on a housing feed-through.

A fluid-tight feed-through for the electric conductors can simultaneously serve as a fastening element for the strain relief element, in the case of a blood pump, but also with another electrical assembly. Such a feed-through for example can consist of metal pins which are moulded into glass or resin and which can be stuck onto the respective crimp sleeves at the ends of the conductors of the cable element. The glass or resin body of the feed-through can additionally serve for moulding or bonding an end of the strain relief element into it, and with this, for fastening the strain relief element on the feed-through and on the housing of the assembly.

The strain relief element, for improving the adhesion on at least one, in particular on both its ends can comprise notches or prominences on its sheath-side periphery.

A further advantageous design of the invention can envisage the conductors of the implantable cable element on at least one of their ends being provided in each case with a crimp sleeve, which can be stuck onto pins of a housing feed-through and/or a plug-in connection element. In a further embodiment, the ends which are provided with a crimp sleeve (then "female" ends) can preferably be stuck in each case into a channel of a housing feed-through and/or into a plug-in connection element. The housing feed-through in some embodiments is an insulating body. It is then only the male plugs which are yet to be inserted into the corresponding channels of the housing feed-through for the completion of the plug-in connecting, in the case of the insertion of the ends.

It is particularly the case when the conductors consist of a quantity of strand wires that these can be connected to a crimp sleeve in the course of a crimp connection, wherein the crimp sleeve can be connected to a plug-in sleeve which can be stuck onto a contact pin. A mechanical and electrical connection of the conductors in each case to a plug-in connection element results with this. The crimp sleeves can advantageously also be soldered to pins on the feed-through or crimped onto these, in the region of the connection of the cable element to the electrical assembly.

A second aspect of the invention envisages the cable sheath of the implantable cable comprising a marking running in its longitudinal direction, as well as a further marking between the plug-in connection element and the end of the layer promoting the ingrowth of tissue. In this manner, it is visible to the operator as to when the cable lies in the tissue in a tension-free manner, without being unnecessarily twisted, when implanting the cable element. The marking on the cable sheath and running in the longitudinal direction indicates this.

In an embodiment of the second aspect, the further marking is a marking which runs transversely to the longitudinal direction and which at a certain defined length of the cable makes it apparent to the operator as to how far the cable is to be implanted and how far for example the layer on the cable element and favouring the ingrowth of tissue reaches, in as much as this is not directly visible due to the design of this layer.

It is ensured by way of the transverse marking that the layer promoting the ingrowth of tissue is not pulled out of the body, but remains completely within the body. The risk of infection is greatly reduced in this manner. With regard to this, an autonomous invention lies in the transverse marking of the cable element, independently of the internal construction of the cable element, and this invention can be combined with the different constructions of the cable element, as are represented in this application. I.e., a transverse marking in combination with a cable element which comprises a section of a layer favouring the ingrowth, wherein the transverse marking is distanced to this section and forms an autonomous which is to say independent invention. On implantation of the cable element, this is implanted in the sterile condition and subsequently at an end lying outside the body is either pulled in a manner until the transverse marking exits from the body, or on implantation one takes care that the transverse marking comes to lie essentially in the region of the exit of the cable element out of the body.

In a further embodiment of the second aspect, the marking running in the longitudinal direction and/or the further marking comprises or consists of an inscription. The inscription for example can contain information as to how far a layer promoting the ingrowth still lies in the patient. By way of this, the cable element can be pulled out of the patient, without the layer favouring the ingrowth being pulled from the body. The risk of infection to the patient can be reduced in this manner. The marking in the longitudinal direction can also be given by an inscription.

In other embodiments, the marking or the further marking comprise graphic elements such as for example a defined colouring or geometric symbols or lines. The graphic elements thereby serve for example as information, as to how far the layer promoting the ingrowth of tissue still lies from the feed-through opening, in the body. One can therefore avoid the layer favouring the ingrowth from being inadvertently pulled out of the body.

In some embodiments, the marking or the further marking comprises haptic elements such as prominences or recesses in the cable sheath. These elements too can represent a distance between the marking and the layer favouring the ingrowth of the tissue.

Although a marking in the longitudinal direction and a further marking were discussed in the previous examples, embodiment examples with only one of the two markings are likewise encompassed by the invention. Thereby, the markings can be realised as discussed above. The electrical arrangement can likewise be formed without a layer favouring the ingrowth. Moreover, the cable sheath can be continuously subjected to a layer favouring the ingrowth or consist of a material favouring the ingrowth or comprise this.

The marking or the further marking can likewise represent a distance between the marking and a certain point of the cable sheath. A length of the cable sheath, which is to remain in the body of a patient, can be reliably determined in this manner, and too far a withdrawal of the cable can be prevented.

The invention moreover relates to an electrical arrangement with a second cable element which comprises a first plug-in connection element for connection to the implantable cable, as well as with a control unit for the activation of the implantable electrical assembly which is connected to the second cable by way of a second plug-in connection.

The concept of connecting an electrical assembly, an implantable cable element, an additional extracorporeal cable element and a control unit via two releasable plug-in connections, on the one hand in the region between the implantable cable element and the extracorporeal cable element, and on the other hand between the extracorporeal cable element and the control element, from the point of view of the invention represents the optimum of reliability and durability on the one hand and practical handling ability on the other hand. The extracorporeal cable (second cable) and the control unit are easily exchangeable by way of this. The total length of the cable connection between the control unit and the assembly can be adapted via the length selection of the extra-corporal cable, when adapting to a patient. The extracorporeal cable which is subjected to a particularly high mechanical loading due to abrupt bending and wear, can moreover be exchanged without problems and adaptation effort.

The invention is hereinafter represented in the drawings and subsequently explained by way of one embodiment example.

FIG. 1 schematically shows an implantable cable element 1 which together with an electrical assembly 2 in the form of a blood pump is implanted in the body 3 of a patient. The line 4 thereby in cross section indicates the surface of the skin of the patient, i.e. the surface and separating surface between the inside and outside of the body. The implantable cable element 1 is thereby fixedly connected at its end 5 inside the body, to the assembly 2. What is meant by this is that no plug-in connection is provided in this region, but that the individual elements of the implantable cable element 1 are connected to parts of the assembly 2 by way of join connections, such as welding, bonding, soldering, crimping or likewise. The types of connection are dealt with in an even more detailed manner further below.

The implantable cable element 1 at its end which is more remote from the assembly 2 comprises a plug-in connection element 6 for creating a plug-in connection 6, 7 to a further plug-in connection element 7 of a second cable element 8. The second cable element 8 connects the implantable cable element 1 to a control unit 9. For this, the second cable element 8 at its end 10 facing the control device comprises a third plug-in connection element for inserting into a socket 11 of the control element 9 which is fixed to the housing. The electrical arrangement thus makes do with two plug-in connections 6, 7 and 10, 11. This leads to the fact that the second cable element 8 which is particularly loaded being able to be exchanged without any problem.

The construction of the first implantable cable element 1 is represented in FIG. 2 in detail and in cross section. This centrally comprises a strain relief element 12 which consists for example of high-strength plastic fibres such as aramide. The strain relief element 12 can be wrapped with a layer 13 of bandages of a plastic foil, in order to simplify the sliding of the conductors 14, 15 which are arranged centrically about the strain relief element 12. The conductors 14, 15, of which eight are present around the tension relief element 12 in the represented example, are in each case individually surrounded by an insulation 14', 15', wherein the insulations apart from effecting the electrical insulation of the conductors to one another also effect a slight sliding to one another, in the case of a bending or movement of the cable element.

The conductors 14, 15 are stranded around the strain relief element 12, in order to achieve a particular flexibility of the cable. Each individual one of the conductors 14, 15 consists of a group of strand wires which for their part can be stranded in one or more concentric layers. Individual strand wires thereby can be inhomogeneous to the extent that they consist of a central silver core with an outer coating of a nickel cobalt base alloy. Alternatively however, the manufacture from a high-strength copper alloy would also be possible as an alternative to this. The conductors of the different layers can be arranged for example with a changing pitch in the case that the conductors are arranged in a multi-layered manner in other embodiment examples.

The conductors as a whole as strand bundles can be provided with a silver layer or gold layer by way of galvanising, in order in the one hand to physically provide a covering of the conductor material and on the other hand to prevent a corrosion due to the particular placement of the noble metals in the electrochemical series.

The stranded group of conductors 14, 15 for its part is covered radially to the outside by a combination of a metal-coated plastic non-woven and a braiding of copper stands, and these form an electrical shielding 41. The strand braiding can thereby be integrated and moulded into the cable sheath as a reinforcement of this. However, it can also be provided radially within the cable sheath.

Materials such as polyurethane and silicones are considered, in order to meet the demands placed on the cable sheath with regard to UV resistance, biocompatibility, wear resistance and mechanical characteristics as well as elasticity. A reinforcement by reinforcement elements such as wire strands, glass fibres or likewise, as well as a covering by a textile layer is possible for this.

The complete length of the implantable cable element 1, beginning from the electrical assembly 2 up to the plug-in connection element 6 is schematically represented in FIG. 3. It is shown that the outside of the cable sheath, in the region, in which the cable element 1 passes through the skin 4 of the patient, is provided with an outer layer which encourages the ingrowth or ongrowth of living tissue and which is represented in FIG. 3 in a dotted manner and is indicated at 16. The layer 16 extends up to an axial region 17 of the cable length which is represented by a dashed line, i.e., the region 16 is distanced to the plug-in connection element 6 in the axial direction, thus does not extent up to the plug-in connection element 6. This prevents germs from settling on the outer cable sheath along the cable length outside the body of the patient, wherein the growth and proliferation of these germs would be encouraged by the roughened structure of the surface of the cable sheath. Optical markings are moreover represented in FIG. 3, of which the first marking 18 is designed as a line which is peripheral around the cable sheath in the peripheral direction and which visibly indicates to the operator, as to a region which must lie outside of the body of the patient.

A dashed line which extends in the axial direction parallel to the longitudinal axis of the cable element along the cable sheath of the implantable cable element is moreover represented as a further marking 19. If the implantable cable element 1 is twisted (kinked), then this it is easily visible to the operator through the helical peripheral running of the dashed line 19, and he can overcome the tension which has arisen due to the kinking of the cable element 1, by way of a corresponding back-twisting. This favours a permanent mounting of the cable element 1 in the body of a patient without any problem.

At a second end of the implantable cable element 1, it is shown that the individual conductors 14, 15 are received in crimp sleeves 20, 21 which can be stuck onto contact pins 22, 23 of a plug-in connection element 6 and can be clamped or soldered there. The plug-in connection element 6 can then be stuck together with a plug-in connection element 7 of a further cable element outside the body of the patient.

The crimp sleeves 20, 21 are connected to the conductors 14, 15 in a mechanically and electrically fixed manner by way of crimping or soldering.

In a further embodiment example, the plug-in connection element 6 can be designed as an insulation body. In this case, the insulation body comprises channels, into which the conductors 14 and 15 provided with the crimp sleeves 20, 21 are inserted. The channels are designed as openings which run through the insulation body and are with a first and second end, wherein the conductors 14 and 15 are inserted into the first end of a channel in each case. In this embodiment example, male pins are inserted into the second end of the channels for connection of the plug-in connection, so that the male pins contact the conductors 14 and 15 in each case.

FIG. 4 in an enlarged scale one again shows the ends of the conductors 14, 15 of the implantable cable element 1 with crimped-on end-sleeves 20, 21 which can be stuck onto contact pins 22, 23 of the plug-in connection element 6. The pins 22, 23 are moulded into an insulating carrier 24 which for example can consist of a resin, and into which an end 25 of the strain relief element 12 can likewise be moulded with a sheath-side thickening or recess. The insulating carrier 24 is moulded or bonded into a plug-in sleeve. The plug-in connection element 7 which is located at the end of the second cable element 8 can be inserted into this plug-in sleeve and stuck onto the plug-in connection element 6. There, corresponding plug-in sleeves 27 are connected to the individual conductors of the second cable element 8 and are fixed in the plug-in connection element 7, which can be stuck onto the contact pins 22, 23.

The cable element 8 for example can have a construction which completely or partly corresponds to the construction of the implantable cable element 1.

Figure 5:
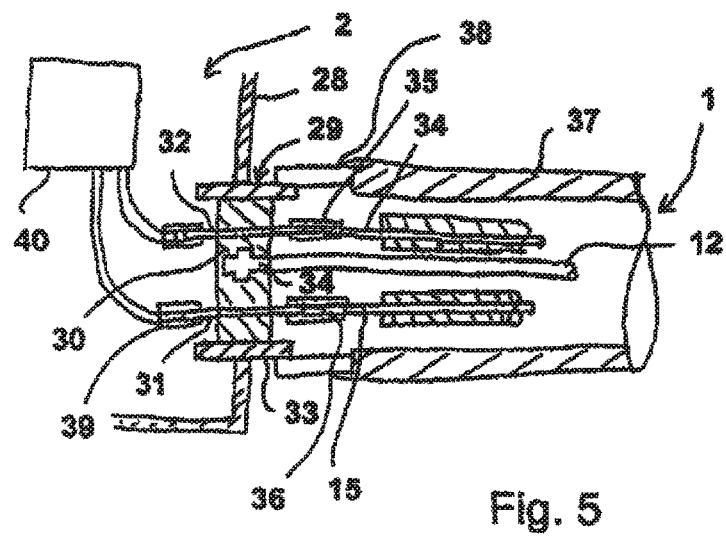

The connection of the implantable cable element 1 onto the housing, more precisely onto a feed-through 29 on the housing 28 of an electrical assembly, in particular of a heart pump, is represented in FIG. 5. The feed-through 29 which comprises a sleeve 33 and a glass body 30 fitted into the sleeve in a gas-tight manner, is represented in the housing wall 28. Continuous contact pins 31, 32 are moulded into the glass body 30 in a fluid-tight manner. An end 34 of the strain relief element 12 which comprises undercuts is moulded into the glass body 30, in order to ensure the coupling of the tensile forces onto the housing of the assembly there. The implantable cable element 1 is effectively relieved of tension by way of this. The conductors 14, 15 of the cable element 1 are fastened in the end-side contact sleeves 35, 36 by way of crimping, wherein the contact sleeves are pushed onto the continuous contact pins 31, 32 and can be soldered to these for example. The cable sheath 37 which represents the outermost layer of the cable element 1, at the end is connected to a union sleeve 38 in the form of a union nut or a bayonet sleeve, which for its part is connected to the sleeve 33 in a fluid-tight manner, by way of bonding or soldering for example. The continuous contact pins 31, 32 at the inner side of the housing 28 are connected via contact locations, for example likewise in the form of crimp sleeves 39, to the connections of an electric element, for example a motor 40.

The represented conductors 14, 15 are merely represented by way of example, and the invention is to be understood to the extent that the number of conductors as well as the transmitted potentials and signals can be fashioned in a varied manner. In the case of a blood pump, conductors for the supply of a magnetic bearing and for transmitting signals can moreover be provided, apart from the conductors for the electric energy supply of the motor 40.

Different variants for fastening the strain relief element 12 to the assembly 2 are represented in the FIGS. 6a to 6d. Hereby, one makes do without a detailed description of the assembly in each case. Details with regard to the assembly can be deduced from the preceding description.

A feed-through 29, which shows the glass body 30 with contact pins 31 and 32 is represented in FIG. 6a. The glass body 30 moreover comprises a web 30a which extends away from the assembly and is with a bore 30b having an opening width permitting a feed-through of the aramide fibres 12. The strain relief element 12 is thereby design in a manner such that it comprises a loop 12a, which is fixed by a crimp sleeve 12b. The loop 12a is threaded through the bore 30b before depositing the crimp sleeve 12b, and the loop is subsequently fixed with the crimp sleeve 12b. The loop can also be knotted, as an alternative to the use of the crimp sleeve 12b.

A feed-through 29 with a glass feed-through 30 and pins 31 and 32 is represented in FIG. 6b. The strain relief element 12 at its end which faces the assembly comprises a knotting 12c, so that a local thickening of the strain relief element 12 takes place at its end. The strain relief element 12 is moulded with a polyamide for example, so that the strain relief element 12 is reliably connected to the glass feed-through. The pins are thereby stuck on first of all and the fibres are aligned, wherein the fibres are preferably aligned subsequent to sticking on the pins, and the moulding mass is subsequently filled in.

The end of the strain relief element 12 is arranged in the region of the glass feed-through and the moulding mass is subsequently filled in, for creating the moulded compound 34. The feed-through can be connected to the assembly after the curing which is to say after the hardening. The feed-through is alternatively already connected to the assembly and the moulding of the strain relief element takes place thereafter.

A further alternative for the connection of the strain relief element 12 to the feed-through 29 is represented in FIG. 6c. The outer side of the feed-through 29 is represented in FIG. 6c. This comprises a bore 29a which is arranged on the side of the glass feed-through which is away from the assembly. An end of the strain relief element 12 is pulled through this bore and this is subsequently either knotted or provided with a crimp sleeve, on the outer side, so that the yarn is pulled tighter around the feed-through 29 given a pull on the strain relief element.

A further alternative is represented in FIG. 6d. Hereby, the feed-through 29 apart from the glass feed-through 30 and the pins 31 and 32 comprises a further insulation body 42 which at its side facing the glass feed-through comprises an opening, through which a strain relief element 12 can be threaded, wherein a knot 12d of the strain relief element prevents the strain relief element from slipping out in a direction which is away from the assembly. The insulation body is thereby stuck onto the glass feed-through and is connected to this with the methods known from the state of the art.

The features of the invention permits the construction of an implantable cable element as well as a corresponding electric arrangement which comprises at least one cable element and, as the case may be, additional elements, in a manner which combines a high reliability with a long service life and a high comfort in application, for the patient.

Different variants of markings are explained in more detail by way of FIG. 7.

Figure 7A:
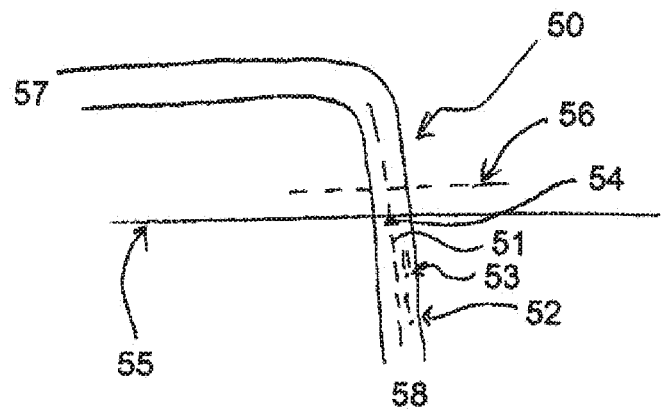

An implantable cable element or a visible cable sheath 50 which comprises a longitudinal marking 51 and further markings 52 to 54 is shown in FIG. 7a. The cable element 50 pierces the skin 55 in the region of the represented marking 54. The cable element 50 with the help of the marking 54 should be prevented from being pulled out further than up to the drawn-in region 56 of the cable element 50. Thereby, the distal end of the cable element is located in the body, and the proximal end 58 is located outside the body. With regard to the further marking 54, it is the case of a triangle which tapers from the proximal to the distal end of the cable element. The tip of the triangle thereby represents a marking, beyond which the cable element should not be pulled out. Further markings 52 and 53 are arranged on the cable element, so that the operator is not surprised by the marking, wherein with regard to these markings, it can be the case of an exclamation mark for the marking 52 and a double exclamation mark in the case of the marking 53. These markings warn the operator that the marking 54 which is decisive for the position of the cable element 54 will be visible next.

The drawn cable element has no layer promoting the ingrowth, but can also comprise a layer which favours the ingrowth and which for example reaches up to the section plane 56. Of course, a cable element 50 which is completely covered by a layer favouring the ingrowth is also possible. Here, the further marking 54 defines a distance to the section plane 56.

Figure 7B:
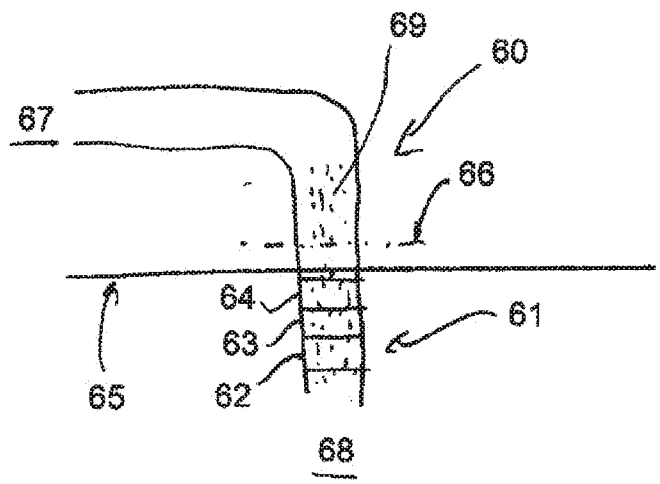

A further embodiment example of different markings is represented in FIG. 7*b*. The cable element 60 comprises a marking system 61 which has markings 62 to 64. An explicit longitudinal marking is not present, but can alternatively also be present. The markings 62, 63, and 64 are tapes held in different colours. Here too, the tapes serve for marking a distance to a section plane 66. By way of this, one is to prevent the section plane 66 not being pulled through the skin 65. It can be recognised as to how the layer 69 favouring the ingrowth is present from the distal end 68 towards the proximal end 67. This layer extends within as well as outside the body. For this reason, the coloured tapes merely define a distance to the section plane 66.

Figure 7C:
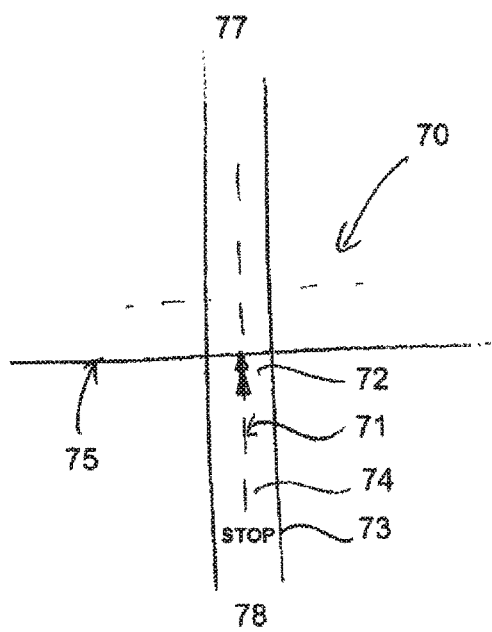

A further embodiment of a cable element is represented in FIG. 7*c*. The cable element 70 comprises a longitudinal marking 71, with the help of which a kinking can be recognised. A double arrow tip 72 which indicates a distance to a predefined section plane is likewise present. An inscription 73 which has the word "STOP" can also be recognised, so as to indicate to the operator the proximity of the double arrow. The operator can end a pull upon the cable as soon as the tip of the double arrow coming from inside the body, has left the skin 75, since the cable element 70 has reached its desired position. The cable element 70 at its proximal end 77 likewise has a layer promoting the ingrowth, as the case may be. This however is not present on the other side of the drawn section plane up to the distal end 78.

Figure 7D:
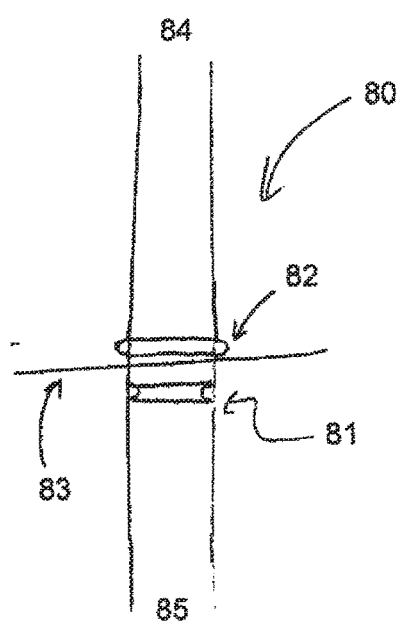

A further embodiment is represented in FIG. 7*d*. The cable element 80 hereby comprises markings 81 and 82 which are designed as haptic elements. Thereby, the marking 81 is designed for example as a peripheral recess in the cable element 80. This marking indicates that a bead-like marking 82 which is to remain in the body, lies distanced to the marking 81 at a defined distance. In this manner, it is ensured that the bead 82 does not penetrate through the skin 83, and moreover an excessive pull upon the distal end 84 is avoided. The proximal end 85 lies outside the body.

LIST OF REFERENCE NUMERALS 1 implantable cable element
2 assembly
3 body
4 skin
5 first end of 1
6 plug-in connection element
7 further plug-in connection element
8 second cable element
9 control unit
10 end of second cable element
11 plug-in sleeve fixed to the housing
12 strain relief element
13 position of bandages
14, 15 conductors
14', 15' conductor insulation
16 region of the cable sheath with ingrowth aid
17 end of 16
18 marking (transverse)
19 marking (longitudinal)
20, 21 crimp sleeves
22, 23 contact pins of 6
24 insulation carrier
25 end
26 plug sleeve
27 plug sleeve
28 housing of an assembly
29 feed-through
30 glass body
31 contact pins of 29
32 contact pins of 29
33 sleeve
34 end of 12
35, 36 contact sleeves
37 cable sheath
38 union sleeve
39 crimp sleeve
40 motor
41 shielding

The invention claimed is:

1. An electrical arrangement with an implantable cable element comprising:
   a group of conductors which are insulated with respect to one another; wherein the implantable cable element comprises a strain relief element which is arranged centrically in the cross section, and the group of conductors which are insulated with respect to one another is stranded around the strain relief element, and a common electrical shielding element which surrounds the electrical conductors is present; and
   a fluid-tight cable sheath.

2. The electrical arrangement of claim 1, wherein the implantable cable element is mechanically and electrically connected in a fixed manner to an implantable electrical assembly.

3. The electrical arrangement of claim 1, wherein the cable sheath of the implantable cable element in sections comprises the layer promoting the ingrowth of tissue.

4. The electrical arrangement of claim 1, wherein the strain relief element consists of plastic fibres.

5. The electrical arrangement of claim 2, wherein the strain relief element is fastened on a housing of the electrical assembly.

6. The electrical arrangement of claim 5, wherein an end of the strain relief element is moulded into or connected onto a housing feed-through.

7. The electrical arrangement of claim 1, wherein the conductors of the implantable cable element are provided at least at one of their ends in each case with a crimp sleeve which can be stuck onto pins of a housing feed-through and/or of a plug-in connection element or can be stuck into the pins and/or the plug-in connection element.

8. The electrical arrangement of claim 2 further comprising: a plug-in connection element for connection to the implantable cable; and a control unit for activating the implantable electrical assembly which is connected to the second cable by way of a second plug-in connection.

9. The electrical arrangement of claim 2, wherein the implantable electrical assembly is a blood pump.

10. The electrical arrangement of claim 3, wherein the layer promoting the ingrowth of tissue is distanced to the plug-in connection element in the longitudinal direction of the cable end.

11. The electrical arrangement of claim 5, wherein the housing of the electrical assembly is a housing feed-through.

12. The electrical arrangement of claim 1, wherein the cable sheath comprises:
   a first marking running in the longitudinal direction of the cable sheath.

13. The electrical arrangement of claim 1, wherein the cable sheath comprises:
   a second marking running in the transverse direction of the cable sheath.

14. The electrical arrangement of claim 12, wherein the first marking is one of a haptic marking, a colored marking, or comprises an inscription.

15. The electrical arrangement of claim 13, wherein the second marking is one of a haptic marking, a colored marking, or comprises an inscription.

16. The electrical arrangement of claim 12, wherein the first marking represents at least a distance between the first marking and the end of the layer promoting the ingrowth of tissue.

17. The electrical arrangement of claim 13, wherein the second marking represents at least a distance between the second marking and the end of the layer promoting the ingrowth of tissue.

\* \* \* \* \*